United States Patent [19]

Arnold

[11] 4,014,335

[45] * Mar. 29, 1977

[54] OCULAR DRUG DELIVERY DEVICE

[75] Inventor: Randall K. Arnold, San Jose, Calif.

[73] Assignee: Alza Corporation, Palo Alto, Calif.

[ * ] Notice: The portion of the term of this patent subsequent to June 8, 1993, has been disclaimed.

[22] Filed: Mar. 25, 1976

[21] Appl. No.: 670,267

Related U.S. Application Data

[60] Division of Ser. No. 569,953, April 21, 1975, Pat. No. 3,961,628, which is a continuation-in-part of Ser. No. 493,819, Aug. 1, 1974, abandoned, which is a continuation of Ser. No. 227,051, Feb. 17, 1972, abandoned.

[52] U.S. Cl. .................................. 128/260; 424/21
[51] Int. Cl.² ........................................ A61M 31/00
[58] Field of Search .......... 128/172, 260, 261, 268, 128/272, 130; 424/19, 21, 28, 22, 30

[56] References Cited

UNITED STATES PATENTS

| | | | |
|---|---|---|---|
| 3,641,237 | 2/1972 | Gould et al. | 128/260 X |
| 3,699,963 | 10/1972 | Zaffaroni | 128/268 |
| 3,710,795 | 1/1973 | Higuchi et al. | 128/130 |
| 3,960,150 | 6/1976 | Hussain et al. | 128/260 |
| 3,961,628 | 6/1976 | Arnold | 128/260 |
| 3,967,618 | 7/1976 | Zaffaroni | 128/130 |
| 3,972,995 | 8/1976 | Tsuk et al. | 428/28 |

*Primary Examiner*—Aldrich F. Medbery
*Attorney, Agent, or Firm*—Paul L. Sabatine; Thomas E. Ciotti; Edward L. Mandell

[57] ABSTRACT

An ocular drug dispensing device for administering a drug at a controlled and continuous dosage unit rate to the eye to produce a local or systemic physiological or pharmacological effect is comprised of a shaped body insoluble in tear fluid and comprised of a first wall, a third wall distant from the first wall, a second wall interposed between the first and third wall and extending around their peripheries for sealingly engaging the first and third wall, a reservoir defined by the inner surfaces of the walls and containing the drug or a mixture of the drug in a carrier and wherein at least one of the first and third walls is formed of an imperforate drug release rate controlling material permeable to the passage of drug or a microporous material containing in the micropores a drug release rate controlling medium permeable to the passage of drug for administering a therapeutically effective amount of drug over a prolonged period of time.

27 Claims, 5 Drawing Figures

OCULAR DRUG DELIVERY DEVICE

CROSS-REFERENCE TO RELATED APPLICATIONS

This application is a voluntary division of United States patent application Ser. No. 569,953 filed on Apr. 21, 1975 now U.S. Pat. No. 3,961,628 which patent is a continuation-in-part of United States patent application Ser. No. 493,819 filed on Aug. 1, 1974 now abandoned, which application is a continuation of United States patent application Ser. No. 227,051 filed on Feb. 17, 1972 now abandoned. These applications are assigned to the same assignee of this application and benefit of their filing dates is claimed.

BACKGROUND OF THE INVENTION

This invention relates to an ocular drug dispensing device for administering a drug to the eye at a controlled and continuous dosage rate.

One of the first ocular devices for dispensing drugs directly to the eye consisted of a lamella of a drug dissolved or dispersed in a water-soluble gel of glycerinated gelatin that was applied to the inner surface of the eyelid. The glycerinated gelatin dissolved rapidly in tear fluid with an accompanying quick release of drug to produce the same kind of effect as liquid dosage forms such as eye drops or ointments. Such lamellae do not provide sustained dispensing and they are not generally used in ophthalmic therapy. See *Remington's Pharmaceutical Sciences*, Ed. XIII, pages 547 to 548, 1965, published by Mack Publishing Co., Easton, Pa., and *An Introduction to Pharmaceutical Formulation*, by Fishburn, page 116, 1965, published by Pergamon Press, Ltd., New York, N.Y.

Recent advances for administering a drug to the eye are disclosed in U.S. Pat. Nos. 3,416,630 and 3,618,604 owned by Applicant. These patents describe ocular inserts that act as a depot or drug reservoir for slowly releasing drug to the eye for prolonged periods of time. The inserts are fabricated of flexible polymeric materials that are biologically inert, non-allergenic, and insoluble in tear fluid. To initiate the therapeutic program, these ocular inserts are placed in the cul-de-sac between the sclera of the eyeball and the eyelid for administering drug to the eye. Since the ocular inserts are formed of polymeric materials that are insoluble in tear fluid, they retain their shape and integrity during the course of the needed therapy to serve as a drug reservoir for continuously administering drug to the eye and the surrounding tissues at a rate that is not affected by dissolution or erosion of the polymeric material. The ocular insert, on termination of the desired therapeutic program, is removed from the cul-de-sac. Thus, the inserts of the above-mentioned patents provide a complete ophthalmic dosage regime for a prolonged period of the time, generally on the order of 24 hours or longer.

The device of U.S. Pat. No. 3,416,530 is manufactured with a plurality of capillary openings that communicate between the exterior of the device and an interior chamber generally defined from a polymeric membrane. While these capillary openings and this construction are effective for releasing drug to the eye, they add considerable complexity to the manufacture of the device because it is difficult to control the size of these openings in large scale manufacturing using various polymers as required for various drugs.

The device of U.S. Pat. No. 3,618,604 does not involve such capillary openings, but instead provides for the release of drug by diffusion through a polymeric membrane at a drug release rate that can be controlled with precision and reproducibility. The device, in a preferred embodiment, as disclosed in that patent, comprises a sealed container having the drug in an interior chamber. While remarkably effective for administering drug, certain problems have been encountered in manufacturing the devices. For example, one problem is the difficult task of sealing the margins of the membrane to form the container. Another problem met in making such device when drug in solid form is contained therein, is the stresses and strains introduced into the membrane walls from deformation during manufacture in forming the reservoir, causing the device, in many instances, to rupture and leak. In addition, this causes entrappment of air and the alteration of the release characteristics of the membrane. A further problem with such devices when used for containing drug in liquid form, is that during manufacture, the liquid spreads and wets the sealable surfaces. These wet surfaces cannot be sealed to make a device essentially free of leaks.

SUMMARY OF THE INVENTION

Accordingly, it is an immediate object of this invention to provide an ocular device for the administration of a locally or systemically acting drug to produce a physiologic or pharmacologic effect which device overcomes the problems of the prior art.

A further object of this invention is to provide a dosage regimen for administering a drug to the eye for a particular time period, the use of which requires intervention only for initiation and termination of the regimen.

Still another object of this invention is to provide an ocular insert which is comfortable to wear for long periods and does not cause discomfort during sleeping and normal daily wear while simultaneously administering drug to the eye.

Yet another important object of the invention is to provide an ocular device of construction and design so as to eliminate unwanted drug leaks and membrane failures during use.

Still a further object of this invention is to provide a process for making such new ocular drug dispensing devices.

Another object of the invention is to provide an ocular device for the controlled release of drug having enhanced mechanical and physical properties.

In accomplishing the objects, features and advantages, the invention is summarized in one aspect as an ocular delivery device for the continuous administration of drug over a prolonged period of time comprising a sealed container shaped for insertion into the eye, the container having a pair of separate and discrete first and third membrane walls spaced from each other, each formed of a material insoluble in tear fluid, with at least one of the membrane walls being permeable to the passage of drug by diffusion at a controlled rate, and a second ring-shaped wall interposed between and sealing engaging the first and third membrane walls along their outer faced peripheries to define an integral unit and form a closed reservoir defined by the inner surfaces of the first, second and third walls, said reservoir containing drug which is released from the reservoir at a controlled rate by passage through the rate controlling membrane wall. The device, in a preferred embodiment, is shaped and adapted for insertion and comfortable placement in the cul-de-sac of the conjunctiva between the sclera of the eyeball and the eyelids.

Other objects, features, and advantages of the invention will be apparent to those skilled in the art from the following detailed description of the invention, taken in conjunction with the drawings, and the accompanying claims.

BRIEF DESCRIPTION OF THE DRAWINGS

In the drawings, which are not drawn to scale, but are set forth to illustrate various embodiments of the invention, the figures are as follows.

In the drawings and specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
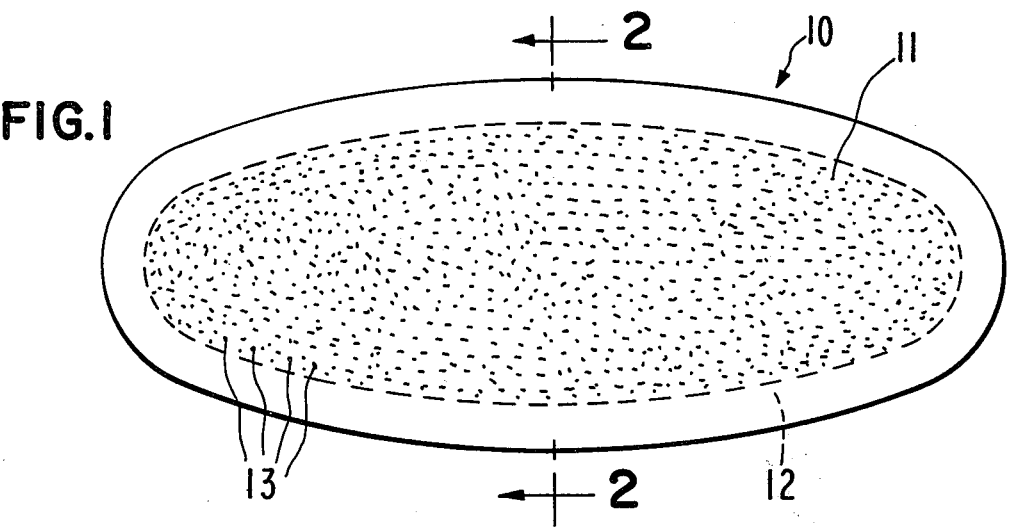
FIG. 1 is a top plan view of an ocular device illustrating the top membrane wall and the annular ring.

Turning now to the drawings in detail, which are examples of ocular devices of the invention, and which examples are not to be construed as limiting, one embodiment of a device is indicated in FIG. 1 by numeral 10. Device 10 is comprised of membrane wall 11 formed of a release rate controlling material permeable to the passage of a drug 14 by diffusion. Wall 11 carries on its inner surface an inner positioned wall 12, schematically illustrated by dashed lines, which wall 12 extends around the perimeter of wall 11 to engage it in sealed relation with another wall, not shown in FIG. 1, distant from wall 11 to form device 10.

Figure 2:
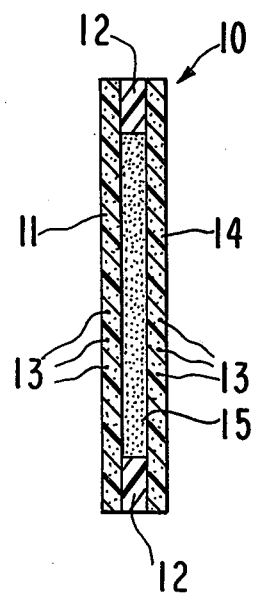
FIG. 2 is an enlarged cross-sectional view of a device depicting the two membrane walls with their interior peripheral surfaces in contact with the surface of the spacer middle wall positioned between the membrane walls.

Referring to FIG. 2, ocular drug delivery device 10 is seen in cross-section along line 2—2 of FIG. 1. As seen in FIG. 2, device 10 is comprised of a first separate and discrete membrane wall 11 and a third separate and discrete membrane wall 14 distant from the first wall 11. Wall 11 and wall 14 bear on their inner surfaces a second wall 12 that extends around the outer perimeter of wall 11 and wall 14 to form a closed reservoir 15. Reservoir 15 contains a drug 13, or a mixture of drugs. Wall 11 and wall 14 can be the same or they can be different and at least one of the walls, 11 or 14, or both of the walls, is comprised of a flexible, substantially homogenous, substantially imperforate drug release rate controlling material permeable to the passage of drug 13 as by diffusion. Alternatively, at least one of the walls, 11 or 14, is comprised of a flexible microporous material, the micropores of which contain a drug release rate controlling medium permeable to the passage of drug 13, as by diffusion. When one of walls 11 and 14 is permeable to the passage of drug 13, the distant wall can optionally be formed of a material essentially impermeable to the passage of drug or of a material permeable to drug of either the homogenous or microporous types described above. Wall 12 of device 10 is formed of a flexible, non-allergenic, biologically inert, material insoluble in tear fluid which is suitable for joining wall 11 and wall 14 together to form an essentially closed reservoir 15 as defined by the inner surfaces of the walls 11, 12 and 14. Drug 13 is preferably in a solid, semi-solid, or gel form, either alone or mixed with a carrier. In the case of drugs which are liquids, such drug is preferably compounded with a gellation agent to form a solid or gel suitable for incorporation in the reservoir 15 as hereinafter described.

The parts of device 10 act in concert as an ocular drug dispensing device to effectively dispense a drug to the eye and to its surrounding tissues at a controlled and continuous rate for a prolonged period of time. When wall 11 or wall 14 is comprised of a material that is substantially homogenous and imperforate, molecules of drug dissolve in and migrate through the material itself by diffusion. When wall 11 or wall 14 is made from a microporous material, molecules of drug migrate by diffusion through a liquid phase present in the pores of the microporous material. Wall 11 or wall 14 may also be made from a material which is both microporous and homogenous. Drug can be released to the eye by diffusion through a diffusive medium within the pores of the material and by diffusion through the polymer as such.

Figure 3:
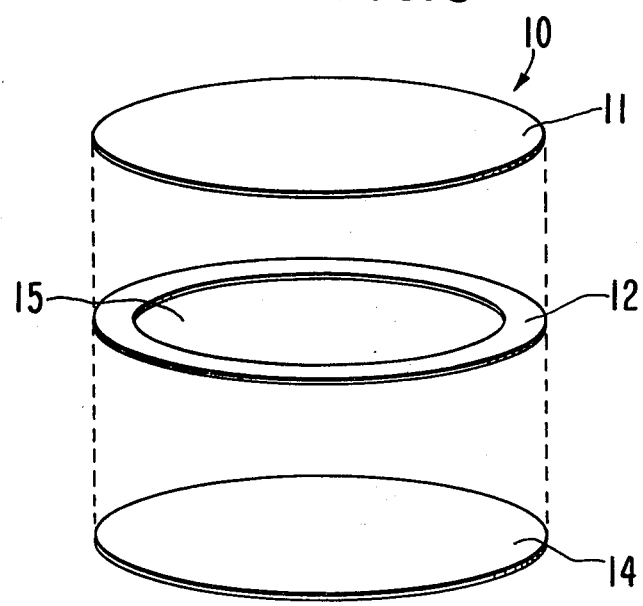
FIG. 3 is an exploded view illustrating the elements prior to their union wherein they act in concert to form an integral device.

Wall 12, positioned between wall 11 and wall 14, functions as a bonding or joining wall used essentially for joining wall 11 and wall 14 in a spaced relationship. Wall 12 is formed of a material that readily lends itself for sealingly engaging wall 11 and 14 to form a flexible, sealed device. Wall 12 may be optionally comprised of a material permeable or impermeable to drug since its exposed surface area in contact with the eye and its surrounding tissues is small compared with the total exposed surface area of walls 11 and 14. The shape of wall 12 as seen from FIG. 3 is "ring-like" and this term is meant to also include elliptical, oval or any other geometric shape which extends around the perimeter of the membrane walls.

Figure 4:
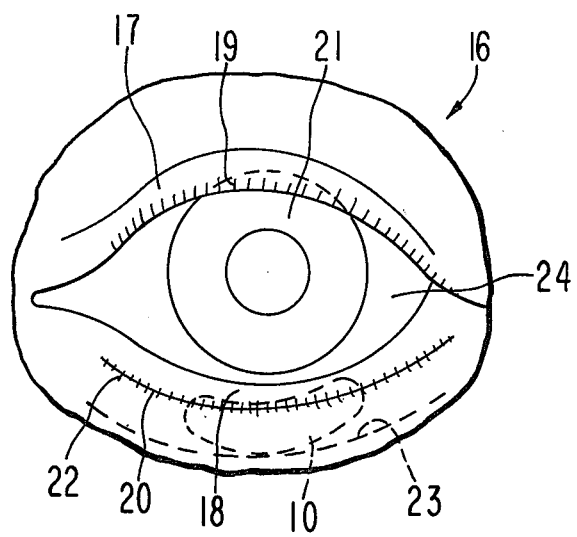
FIG. 4 is a partly diagrammatic, front elevational view of a human eye illustrating an ocular device in operative position after its insertion into the eye.

Referring to FIG. 4, device 10 is shown positioned in immediate contact with an eye 16 for administering a drug thereto. Eye 16 is comprised of an upper eyelid 17 with eyelashes 19 at the edge of eyelid 17 and a lower eyelid 18 with eyelashes 20 at the edge of eyelid 18. Eye 16 anatomically is comprised of an eyeball 22 covered for the greater part of its posterior area by a sclera 24 and at its central area by a cornea 21. Eyelids 17 and 18 are lined with an epithelial membrane or palpebral conjunctiva, not shown, and sclera 24 is lined with a bulbar conjunctiva which covers the exposed surface of eyeball 22. Cornea 21 is covered with a transparent epithelial membrane, not shown. The portion of the palpebral conjunctiva which lines upper eyelid 17 and the underlying portion of the bulbar conjunctiva defines an upper cul-de-sac, not seen in FIG. 4, while that portion of the palpebral conjunctiva which lines lower eyelid 18 and the underlying portion of the bulbar conjunctiva define a lower cul-de-sac, not seen in FIG. 4. Device 10 may be shaped and sized for insertion in the cul-de-sac of the conjunctiva between sclera 24 of eyeball 22 and upper eyelid 17, or as seen in broken continuous line, may be shaped and sized for positioning in the cul-de-sac of the conjunctiva between the sclera 24 of eyeball 22 and lower eyelid 18, generally to be held in position by the natural pressure of the respective eyelid.

Figure 5:
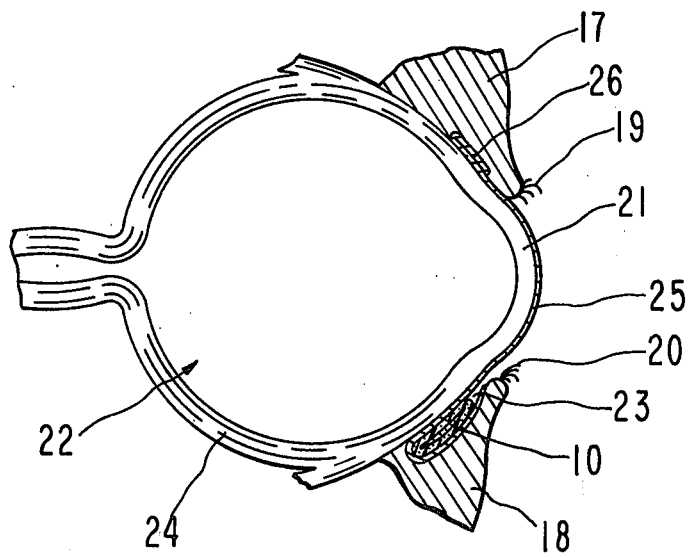
FIG. 5 is a view partly in vertical section and partly diagrammatic of an eyeball and the upper and lower eyelids associated therewith showing the ocular insert in operative position.

In FIG. 5, eye 16 is shown in horizontal section with device 10 in position to dispense drug. Eye 16 is comprised of upper eyelid 17 and lower eyelid 18, with their respective eyelashes 19 and 20, eyeball 22, cornea 21 and sclera 24. An upper cul-de-sac 26 and a lower cul-de-sac 23 are defined by a conjunctiva 25. Device 10 is positioned in lower cul-de-sac 23 to continuously dispense a predetermined amount of drug or a combination of drugs from the device to the eye and its surrounding tissues over a prolonged period of time. In operation, after drug leaves the device, it is transported to the eye and its surrounding tissues, by physiological processes such as the flow of tear liquid and blinking action of the eyelids.

DETAILED DESCRIPTION OF THE INVENTION

In accordance with the practice of the invention, it has been found the device of this invention provides many important advantages over previously known ocular drug delivery devices. One advantage of the device is the ease of construction by standard manufacturing techniques into devices of various sizes, shapes and forms. For example, the device can be of any convenient geometric shape for comfortable retention in the eye. Typical shapes include ellipsoid, bean-shaped, banana-shaped, circular-shaped, rectangular-shaped, trapezoidal and doughnut-shaped. In cross-section, it can be doubly convex, concavo-convex, and rectangular as the device during use, will tend to conform to the configuration of the eye. The dimensions of the device can vary with the size of the device, the amount of drug in the device's reservoir, the membrane which governs the rate drug is to be administered, and by the size of the eye. Satisfactory devices generally have a length of 4 to 20 millimeters, a width of 1 to 15 millimeters, and a thickness of 0.1 to 4 millimeters, a reservoir with a diameter of 1.2 to 14.8 millimeters, and contain from 1 microgram to 100 milligrams of drug or more.

Materials suitable for fabricating the wall(s) of the imperforate, substantially homogenous type described above, include naturally occurring or synthetic materials that are biologically compatible with body fluids and eye tissues, and essentially insoluble in body fluids with which the material will come in contact. The use of rapidly dissolving materials or materials highly soluble in eye fluids is to be avoided since dissolution of the wall would affect the constancy of the drug release, as well as the capability of the system to remain in place for a prolonged period of time. Exemplary naturally occurring or synthetic materials suitable for fabricating such walls are poly(methylmethacrylate), poly(butylmethacrylate), plasticized poly(vinylchloride), plasticized nylon, plasticized soft nylon, plasticized poly(ethylene terephthalate), natural rubber, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), poly(trifluorochloroethylene), chlorinated poly(ethylene), poly(4,4'-isopropylidene diphenylene carbonate), ethylene-vinyl acetate copolymer, plasticized ethylene-vinyl acetate copolymer, vinylidene chlorideacrylonitrile copolymer, vinyl chloride-diethyl fumerate copolymer, silicone rubbers, especially the medical grade poly(dimethylsiloxanes), ethylene-propylene rubber, silicone-carbonate copolymers, vinylidene chloride-vinyl chloride copolymer, vinyl chloride-acrylonitrile copolymer and vinylidene chloride-acrylonitrile copolymer.

As stated above, such homogenous imperforate materials dispense drug by a process of diffusion. In that process, the drug dissolves and equilibrates in the material at the inner surface of the wall, and then diffuses in the direction of lower chemical potential, i.e., toward the exterior surface of the wall. At the exterior surface of the wall, equilibrium is again established. When the conditions on both sides of the wall are maintained constant, a steady state flux of the drug will be established in accordance with Fick's Law of Diffusion. The rate of passage of the drug through the material by diffusion is generally dependent on the solubility of the drug therein, as well as on the thickness of the wall. This means that selection of appropriate materials for fabricating the wall will be dependent on the particular drug to be used. By varying the composition and thickness of the wall, varying dosage rates per area of the ocular device can be obtained.

Materials of the microporous type suitable for fabricating the wall(s) have pores which range in size from several angstroms, usually at least about 10A, to several hundred microns, but usually not more than about 100 microns. The porosity of these materials may range between about 5 percent and about 95 percent. Exemplary microporous materials are regenerated, insoluble, nonerodible cellulose, acylated cellulose, esterified celluloses, cellulose acetate propionate, cellulose acetate butyrate, cellulose acetate phthalate, cellulose acetate diethyl-aminoacetate, poly(urethanes), poly(carbonates), microporous polymers formed by coprecipitation of a polycation and a polyanion as described in U.S. Pat. Nos. 3,276,589; 3,541,005; 3,541,006 and 3,546,142, modified insoluble collagen, cross-linked poly(vinyl alcohol) with a pore size 7 to 50 A, epoxy resins and poly(olefins) or poly(vinylchlorides) with a pore size of about 50 A or less to 150 microns or larger as conveniently made by leaching out incorporated salts, soap micelles, starch or like materials to give a microporous membrane. Also, the materials that can be used include those materials having homogenous properties and microporous properties, such as cross-linked gelatinous membranes. As indicated above, such microporous materials dispense drug by a process in which the drug diffuses through a diffusive medium in the pores of the material. In this process, the drug molecules dissolve in the medium at the interior surface of the wall and flow through the medium in a direction of lower chemical potential, that is, to the exterior surface of the wall. A drug will have a definite and characteristic rate of diffusion through the diffusive medium which is generally dependent on the solubility of the drug in the diffusive medium, the thickness and porosity of the release rate controlling material and the tortuosity factor.

The diffusive media suitable for use with the microporous materials are those materials which are nontoxic in the eye and surrounding tissues and in which the drug has a limited solubility so that the drug is released by diffusion rather than by simple dissolution which is difficult to control. By "limited solubility" is meant that drug is soluble in given selected amounts in the diffusive medium and includes solubilities such as soluble, sparingly soluble, slightly soluble, very slightly soluble, and almost practically insoluble. Generally, the term limited solubility comprises a range of solubility of drug in medium of from 10 parts per million to 10,000 parts per million on a weight basis.

The medium can be a liquid, a gel, a colloidal solution, a sol, and the solution can be polar, semi-polar, or non-polar. Representative mediums are saline, glycerin, ethylene glycol, propylene glycol, water, emulsifying and suspending agents such as methyl cellulose mixed with water, mixtures of propylene glycol monostearate and oils, gum tragacanth, sodium alginate, poly(vinyl pyrrolidone), poly(oxyethylene stearate), fatty acids such as linoleic, and silicone oil. Other representative mediums are set forth in *Remington's Pharmaceutical Sciences*, pages 246 to 269 and 1338 to 1380, 1970, published by Mack Publishing Company, Easton, Pa.

The diffusive medium can be added to the microporous material by methods well known to the art, for example, by immersion of the material in a bath containing the diffusive medium to let the medium partially fill or fully saturate the micropores of the material. Another method for charging the micropores with a diffusive medium is to add the diffusive medium or a mixture of diffusive media with the drug formulation so that the medium can flow from within the reservoir into the pores and remain therein to permit diffusive flow of drug. In a preferred aspect, the diffusive medium is an isotonic solution such as lachrymal fluid which can be incorporated into the pores of the microporous material by way of the previously described methods or advantageously incorporated by contact with the eye at the time the ocular device is inserted in the eye, in which case, these fluids are available for subsequent transfer into the micropores of the material for functioning as a diffusive medium for drug.

Materials suitable for forming the second wall that is interposed between the first and third walls and sealingly joins the same at their perimeters are naturally occurring and synthetic materials that can serve as a cold setting adhesive or as a hot setting adhesive with tackiness while simultaneously retaining their polymeric integrity to serve as the middle wall and assist the two spaced walls in defining the reservoir. The phrase "cold setting adhesive" as used herein indicates polymeric materials that are tacky and will bond other polymeric materials at set temperatures from 5° to 50° C, and the phrase "hot setting adhesive" is used to indicate a polymeric material that is tacky and will bond other polymers at set temperatures from 50° to 250° C. The term "tacky" generally indicates stickiness of a polymeric material to intimately bond two walls together. The operable temperatures for such bonding polymers can easily be ascertained by standard techniques as set forth in *Modern Plastic Encyclopedia*, Vol. 46, No. 10A, 1969, and in *ASTM Standards*, Structural Sandwich Constructions, Part 16, T. Peel Test: ASTMD 1876-61 T. Peel Resistance, 1965, published by the American Society for Testing and Materials, and like references. Exemplary materials are poly(vinylacetate), cross-linked poly(vinyl alcohol), cross-linked poly(vinylbutyrate), ethylene-ethyl acrylate copolymer, poly(ethyl hexylacrylate), poly(vinylchloride), poly(vinyl acetals), plasticized ethylene-vinyl acetate copolymer, poly(vinyl alcohol), poly(vinylacetate) ethylene-vinylchloride copolymer, poly(vinylesters), poly(vinylbutyrate), poly(vinylformal) and polyamides.

The use of an intermediate second wall in the devices provides several advantages. It enables easy manufacture of a sealed container from materials of different drug diffusion properties. Also colors, that is dyes, may be incorporated into the second wall to serve to identify different drugs, different sized devices and dates of manufacture. Additionally, the dye is not mixed with the drug so potential dye-drug complexes are avoided. Another important advantage of the middle wall is its ability to function as an adhesive to seal together at low temperatures like walls or unlike walls into a composite article of manufacture. Thus, walls formed of materials like poly(vinylchloride) that would require a high sealing temperature, e.g., 200° C or higher, can be hermetically sealed by using a middle wall of, for example, ethylene-vinyl acetate copolymer that serves as a hot melt adhesive to join the first and third walls at a much lower temperature. Additionally, the middle wall by functioning as a hot melt adhesive, can be used to seal generally unsealable walls, for example, walls formed of unplasticized cellulose acetate. Sealing at low temperatures also protects the drug from exposure to high temperatures that could alter or adversely affect the drug.

Still another important advantage obtained by the use of the middle ring-shaped wall is the desirable physical and mechanical properties imparted thereby to the device by substantially eliminating entrapped air and unwanted stresses and strains introduced into the membrane walls during manufacture that lead to ruptures and leaks during use. The elimination of such stresses and strains enhances the flexibility of the device, thereby increasing its ability to be retained in the eye. In addition, the achievement of precision release of drug from the device is made possible by the inclusion of the middle annular wall. This is so since the elimination of unwanted stresses and strains enables the membrane walls to be of uniform characteristics necessary to obtain the desired degree of control over the kinetics of drug release.

As used herein, the term "drug" broadly means compositions administrable to the eye and its surrounding tissues to produce a local or a systemic physiologic or pharmacologic beneficial effect. Examples of drugs include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; antivirals, including idoxuridine; and other antibacterial agents such as nitrofurazone and sodium propionate; antiallergenics such as antazoline, methapyriline, chlorpheniramine, pyrilamine and prophenpyridamine; anti-infammatories such as hydrocortisone, hydrocortisone acetate, dexamethasone, dexamethasone 21-phosphate, fluocinolone, medrysone, prednisolone, methylprednisolone, prednisolone 21-phosphate, prednisolone acetate, fluoromethalone, betamethasone and triaminolone; decongestants such as phenylephrine, naphazoline, and tetrahydrazoline; miotics and anticholinesterases such as pilocarpine, eserine salicylate, carbachol, di-isopropyl fluorophosphate, phospholine iodide, and demecarium bromide; mydriatics such as atropine sulfate, cyclopentolate, homatropine, scopolamine, tropicamide, eucatropine, and hydroxyamphetamine; and sympathomimetics such as epinephrine.

Generally, an ocular drug delivery device will contain from 1 microgram to 100 milligrams of drug or more, for releasing the drug to the eye at art known dosage rates. For example, an ocular drug delivery device can administer 5 to 200 micrograms per hour of pilocarpine and its derivatives for 24 hours to an adult human, or for simultaneous administration of 5 to 120 micrograms of pilocarpine hydrochloride and 10 micrograms to 0.5 milligrams of hydrocortisone acetate for a daily dose, and the like as described in *Physicians' Desk Reference*, Drug Classification Index, Ophthamologicals, page 217, and entries cited therein, 24th Edition, 1969, Medical Economics, Inc.

Drugs can be in various forms, such as uncharged molecules, components of molecular complexes, or non-irritating, pharmacologically acceptable salts such as hydrochloride, hydrobromide, sulfate, phosphate, nitrate, borate, acetate, maleate, tartrate and salicylate. For acidic drugs, salts of metals, amines, or organic cations, for example, quaternary ammonium can be employed. Furthermore, simple derivatives of the drugs such as ethers, esters, amides, and the like, which have desirable retention, release, or solubility characteristics, and which are easily hydrolized by body pH, enzymes, or other metabolic processes, can be employed.

The drug is desirably present in the interior reservoir defined by the walls of the device in a manner, mode and quantity in which it will be in intimate contact, at a constant thermodynamic activity, with the drug-permeable wall(s) of the device throughout the administration period. For this purpose, and for fabricating convenience, it will preferably be present together with a drug-permeable solid or semi-solid (e.g., a gel or colloid) carrier which provides a formulation which may be cast or otherwise formed into a body which may be readily handled and assembled in combination with the walls. In this regard, it is possible to use liquid drugs or liquid drug formulations in the devices of this invention. However, the use of such liquids presents greater handling and assembling problems than the use of solid or gelled materials. It has been found that when the drug is in a liquid form, it is preferable to compound or mix the drug with a gel-forming agent. The agents are used for gellation of liquid drugs for improving the handling, filling and sealing of the device. By gelling a liquid drug to a film, suspension or solid, it is easier to handle and place drug into a reservoir. The solid or film is formed by mixing a gel-forming agent with the liquid drug, followed by shaping to fit the reservoir; or, the reservoir can be filled with the mixture immediately before gellation with the latter occurring in situ. The gel-forming agents can be of naturally occurring or of synthetic origin, and either hydrophobic or hydrophilic. The agent can be a polysaccharide such as a linear neutral or a branched neutral polysaccharide, or a polysaccharide with basic, carboxyl or other acid groups such as a natural gum, a seaweed extract, a plant exudate, a seed gum, a plant extract, or an animal extract, or a biosynthetic gum. Typical gel-forming agents include agar, agarose, algin, sodium alginate, potassium alginate, carrageenan, kappa-carrageenan, lambda-carrageenan, fucoidan, furcellaran, laminaran, hypnea, eucheuma, gum arabic, gum ghatti. gum karaya, gum tragacanth, guar gum, locust bean gum, guince psylluim, flax seed, okra gum, arabinoglactin, pectin, xanthan, scleroglucan, dextran, anylose, amylopectin, dextrins, and synthetic gel-formers such as methylcellulose, hydroxylalkyl derivatives of cellulose wherein the alkyl is 1 to 7 carbons, ethylhydroxyethylcellulose, and sodium carboxymethylcellulose.

To readily maintain such thermodynamic activity, the drug should have limited solubility in the carrier and be present in sufficient excess to initially saturate the carrier and maintain such saturation during the drug administration period. By "limited solubility" is meant that drug is soluble in given amounts in the carrier, that is, it comprises varying concentrations of drug dissolved in the carrier. In most instances, the drug will be soluble in the carrier in amounts ranging between 10 and 10,000 p.p.m. As indicated above, there is also an excess amount of undissolved drug present in the carrier. The initial fractional amount of drug dissolved in the carrier will usually be in the range of 0.1 to 35 percent by weight of the total amount of drug. In any event, there should be sufficient undissolved drug incorporated to serve as a reserve source of drug for replacing released drug by dissolving in the carrier to keep the concentration during the history of the ocular device, or until the ocular device is no longer used. Examples of solid and semi-solid carriers are gelatin, starches, carbohydrates, solid extracts, cured polymers, silicone carbonate copolymers, plasticized polymers, hydrophilic polymers such as hydrophilic hydrogels of esters of acrylic acids, modified collagen, surface treated silicone rubber, alginic acid and derivatives thereof, pectin and plasticized poly(vinylchloride). The carrier can also contain adjuvants such as preserving, stabilizing, or wetting agents.

The materials forming the drug-permeable wall and the carrier are preferably chemically and structurally different within a single device. The permeability of the wall to drug should be lower than is the permeability of the carrier to drug to ensure that release kinetics of the device are controlled by the wall.

The carrier-drug mixture may be prepared by standard mixing techniques such as ballmilling, calendering, shaking and rollmilling.

The process for making the above-described ocular drug dispensing devices comprises:

forming a first wall from a material insoluble in tear fluid and optionally permeable to drug at a predetermined rate and in a shape and size adapted for insertion in the eye;

forming a second wall from a material insoluble in tear fluid in a ring shape having an outer perimeter of generally the same shape as the perimeter of the first wall;

placing the second wall on the first wall with the outer perimeter of the second wall in general registry with the perimeter of the first wall;

charging drug onto the surface of the first wall in the area thereof bounded by the inner perimeter of the second wall;

forming a third wall from a material insoluble in eye fluid and optionally permeable to drug at a predetermined rate, with the proviso that at least one of the first and third walls is permeable to drug at a predetermined rate, in the same general shape as the first wall;

placing the third wall over the drug with its perimeter in general registry with the outer perimeter of the second wall and its periphery contacting said second wall; and sealing the first and third walls to the second wall.

When the drug is of a liquid nature, it is preferred to mix or react the drug with a gelling agent as heretofore described, to form a solid composition prior to charging the formulation onto the surface of the first wall.

Thus, more particularly and in accordance with the above, the device may be assembled by standard procedures such as by molding or casting the first wall, pressing the second annular wall thereto, extruding drug into the reservoir, then sealing the third wall in place as shown in the drawing. The walls can be sealed together by various methods such as high frequency electronic sealing that provides clean edges and firmly sealed ocular devices. By using, for example, high frequency sealing, the wall-forming materials flow-melt at the point of contact to suitably join the walls into a composite article of manufacture. The ability to design and shape the walls into an ocular device of highly reproducible shapes, readily results in fabrication of ocular drug delivery devices with reproducible dispensing properties and thus overcomes a significant disadvantage of previously described devices. Other standard manufacturing procedures are described in *Modern Plastics Encyclopedia*, Vol. 46, pages 62 to 70, 1969, and may be readily adapted by those skilled in the art to fabricate the ocular device of the invention.

The rate of release of a drug through various materials in the pores of the microporous wall can be easily determined by those skilled in the art by standard procedures, as described in *Encycl. Polymer Science and Technology*, Vols. 5 and 9, pages 65 to 82 and 794 to 807, 1968, and the references cited therein, in *Membrane Science and Technology*, by Flinn, James E., pages 16 to 32 and 120 to 138, 1970, published by Plenum Press, Inc., and in *Chemical Engineers Handbook*, pages 17–42 to 17–45, 1963, published by McGraw Hill, Inc. One applicable method employs Fick's Law of Diffusion, wherein the flux of drug through a convection-free medium, for example, a liquid present in a porous membrane, is given by the equation:

$$J = \frac{-\epsilon D}{\tau} \frac{dc}{dX}$$

wherein $J$ is the flux in $gm/cm^2$ sec., $\epsilon$ is the porosity in $cm^3/cm^3$, $\tau$ is the tortuosity factor, $D$ is the diffusion coefficient $cm^2$/sec., and $dc/dX$ is the drug concentration gradient across the barrier.

Thus, when the diffusion coefficient is assumed to be independent of concentration, and the concentration at the outside surface is negligibly small, the equation can be expressed as follows:

$$J = \frac{\epsilon D}{\tau} \frac{C_s}{l}$$

wherein $C_s$ is the saturation solubility of the drug in the diffusive medium, and $l$ is the barrier thickness.

The diffusion coefficient $D$ will be in the order of $2 \times 10^{-6}$ $cm^2 sec^{-1}$ when the drug has a small molecular diameter, for example, about 10 A and the pore diameter of the microporous wall is large in comparison with the molecular drug diameter, for example, at least greater by a factor of 10. However, when the pore diameter of the rate controlling membrane is reduced relative to that of the molecular drug diameter, for example from 10 to about 3 times the molecular diameter, the diffusion coefficient $D$ will decrease to values as low as $2 \times 10^{-8}$ $cm^2 sec^{-1}$. When the ratio of membrane pore diameter to molecular drug diameter significantly is below about 3, the membranes are considered to be homogenous solution diffusion materials. By varying pore diameter or porosity of the microporous materials, substantial changes in release rate can be brought about while still using the same materials.

The rate of release of a drug through various homogenous walls can be determined by standard procedures. In this manner, particular imperforate materials used as the device's wall for the release rate controlling barriers can be selected. Various techniques, such as the transmission method and the sorption-desorption method, can be used as measurers of permeability. One technique that has been found to be well suited is to cast or hot press a film of the material to a thickness in the range of 2 to 60 mils. The film is used as a barrier between a rapidly stirred (e.g., 150 r.p.m.) saturated solution of the drug and a rapidly stirred solvent bath, both maintained at constant temperature (typically 37° C). Samples are periodically withdrawn from the solvent bath and analyzed for drug concentration. By plotting the drug's concentration in the solvent bath versus time, the permeability constant P of the material is determined by the Fick's First Law of Diffusion.

$$\text{Slope of plot} = \frac{Q_1 - Q_2}{t_1 - t_2} = P \frac{AC}{h}$$

wherein $Q_1$ = cumulative amount of drug in solvent in micrograms at $t_1$, $Q_2$ = cumulative amount of drug in solvent in micrograms at $t_2$, $t_1$ = elapsed time to first sample, i.e., $Q_1$, $t_2$ = elapsed time to second sample, i.e., $Q_2$, $A$ = area of membrane in $cm^2$, $C$ = initial concentration of drug, $h$ = thickness of membrane in cm.

By determining the slope of the plot, i.e.

$$\frac{Q_1 - Q_2}{t_1 - t_2},$$

and solving the equation using the known or measured values of $A$, $C$, and $h$, the permeability $P$ constant in $cm^2$/time of the material for a given drug is readily determined. The rate of drug release through different release rate controlling materials can be easily determined by those skilled in the art by standard procedures, as described in *Encycl. Polymer Science and Technology*, Vols. 5 and 9, pages 65 to 82 and 794 to 807, 1968, and the references cited therein, in *J. Pharm. Sci.*, Vol. 52, pages 1145 to 1149, 1963, ibid., Vol. 53, pages 798 to 802, 1964, ibid., Vol. 54, pages 1459 to 1464, 1965, ibid., Vol. 55, pages 840 to 843 and 1224 to 1239, 1966, *Encycl. Polymer Science and Technology*, Vols. 5 and 9, pages 65 to 82 and 794 to 807, 1968, and the references cited therein.

The solubility of a drug in a diffusive medium can be determined by art known techniques. One method consists in preparing a solution of the drug and ascertaining by analysis the amount of drug present in a definite quantity of the medium. A simple apparatus for this purpose consists of a test tube fastened upright in a water bath maintained at constant temperature. The medium and drug are placed in the tube and stirred by a motor driven rotating glass spiral. After a given period of stirring, a known weight of the medium is analyzed and the stirring continued for an additional period of time. If the analysis shows no increase of dissolved substance after the second period of stirring, the results are taken as the degree of solubility of the drug in the medium. Numerous other methods are available for the determination of the degree of solubility of a drug in a liquid medium. Typical methods used for the measurement of solubility are chemical analysis, measurement of density, refractive index and electrical conductivity. Details of various methods for determining solubilities are described in United States Public Health Service Bulletin No. 67 of the Hygienic Laboratory, *Encycl. of Science and Technology*, Vol. 12, pages 542 to 556, 1971, McGraw-Hill, Inc., *Encyclopaidic Dictionary of Physics*, Vol. 6, pages 545 to 557, 1962, Pergamon Press, Inc., and the like.

The solubility of the drug in the carrier is determined by preparing a saturated solution of drug and ascertaining, by analysis, the amount present in a measured area of the carrier. For example, the solubility of the drug in the carrier is determined by first equilibrating the carrier with a saturated solution of the drug at a known temperature, for example 37° C, or with a pure liquid drug, if the drug is a liquid at 37° C. Next, drug is desorbed from the saturated carrier with a suitable solvent for the drug. The resultant solution is analyzed by standard techniques such as ultraviolet, visible spectrophotometry, refractive index, polarography, and electrical conductivity, and from data calculating the concentration or solubility of the drug in the solid carrier.

The diffusion coefficient of a drug is determined by measuring the rate a drug transfers from one chamber through a sintered glass filter of known pore size and thickness into another chamber and calculating from the obtained data the drug transfer rate. The method when used for a diffusive medium, is carried out by adding to a first conical flask equipped with a ground glass stopper and a stirring bar, a measured amount of medium and simultaneously, the drug in the same medium is added to a second concial flask while keeping the level of the medium in the two flasks the same. Next, the flasks are stirred, the samples drawn at various time intervals for analysis. The measured rate of drug transport through the sintered glass filter, and the concentration difference of the drug in the two flasks is then calculated. These procedures are known to the art in *Proc. Roy. Sci. London*, Ser. A, Vol. 148, pages 1935, *J. Pharm. Sci.*, Vol. 55, pages 1224 to 1229, 1966 and references cited therein. The diffusion coefficient of a drug in the solid carrier also can be experimentally determined by using the above apparatus or similar apparatus and procedures as described in *Diffusion in Solids, Liquids and Gases*, by Jost, W., Chapter XI, pages 436 to 488, 1960, Revised Edition, Academic Press, Inc., New York.

The solubility of the drug in the release rate controlling material comprising the homogenous wall is determined by preparing a saturated solution of a given drug and ascertaining the amount present in an area of the material. For example, the solubility of the drug in the homogenous wall is determined by first equilibrating the wall material with a measured saturated solution of the drug at a known temperature and pressure, for example 37° C and 1 atmosphere. Next, drug is desorbed from the saturated homogenous material with a suitable solvent. The resultant solution for the drug then is analyzed by standard techniques such as ultraviolet, visible spectrophotometry, refractive index, polarography, and electrical conductivity. From the data obtained, the concentration or solubility of the agent in the material is calculated.

The following examples are merely illustrative of the present invention and they should not be considered as limiting its scope in any way.

EXAMPLE 1

An ocular drug dispensing device of elliptical shape and comprised of two outer drug release rate controlling walls each fused to an inner middle wall having a center area defining a space and which middle wall extends around the interbonds the internal perimeter of the two outer walls to form an ocular drug dispensing device having a reservoir for contining a drug defined by the internal surfaces of all the walls is manufactured as follows: first, a uniform wall material is formed by dissolving commercially available ethylene-vinyl acetate copolymer in methylene chloride in a concentration ratio or 20 percent copolymer to 80 percent solvent and film casting the solution onto a glass substrate. The solvent is allowed to evaporate at room temperature and the film warm air dried to yield a film about $1.7 \pm 0.2$ mils thick. Two walls, about 16 mm $\times$ 6.75 mm, are pressed from the film for use as the drug release walls of the ocular device. Next, a middle wall is prepared by mixing ethylene-vinyl acetate copolymer, methylene chloride and Food Drug and Cosmetic blue lake dye in a percent ratio of 20 to 80 to 0.1 and the ingredients thoroughly mixed in a commercial, laboratory v-blender. The mixture is cast onto a glass surface, and the solvent evaporated at room temperature. Then, the film is warm air dried to yield a film 4.2 $\times$ 0.3 mils thick. Next, this film is press-cut into an ellipse having the same dimensions of the just press-cut walls. The middle wall is press-cut with the center area punched out to yield a continuous ellipse defining an opening. Then, onto one of the drug release walls is placed a middle wall and these two walls placed into a conventional standard vacuum laminator. Next, a vacuum is pulled to 74 cm. of mercury and held for three minutes. At the end of three minutes, a high flux radiant heater is positioned over the walls and heated for about 15 seconds or until the temperature reaches about 70° C. At the end of the heating, a pressure head is applied to the walls and a pressure of 6.8 Kg. applied for 45 seconds to firmly seal the two walls, and the vacuum released.

Next, to 500 grams of sterile, distilled water is added 300 grams of pilocarpine base and 25 grams of alginic acid and the ingredients well mixed in a standard v-blender, and following the mixing, cast on a clean glass plate. The water is evaporated at room temperature to yeild an alginic acid-pilocarpine drug core, of approximately 92.3 percent pilocarpine base and 7.7 percent alginic acid. A $7.0 \pm 1.0$ mg aliquot of the drug core is then deposited into the two wall laminate, and the third wall placed in contact with the middle wall. The three walls are then vacuum heat laminated as just described to produce a composite article of manufacture. The resulting device, when placed into an adult human eye, will administer 50 micrograms of pilocarpine per hour for 24 hours.

EXAMPLE 2

An ocular drug delivery device for the continuous and controlled rate of drug administration over a prolonged time is manufactured from drug release rate controlling material insoluble in eye fluid according to the procedure as described in Example 1 with the drug reservoir in this embodiment comprised of pilocarpine and alginic acid wherein the ratio of pilocarpine to alginic acid is from 12 to 1 and from 3 to 1 for the controlled release of the drug to the eye.

EXAMPLE 3

An ocular device for the prolonged administration of drug is made according to the procedure of Example 1 with the pilocarpine alginic acid film prepared as follows: first, pilocarpine-free base is dissolved in freshly prepared deionized water. To this is added a stoichiometric amount of alginic acid and the mixture stirred until a viscous, homogenous solution is obtained. An excess of pilocarpine is then added and the solution cast onto a glass plate, doctor-bladed to the desired thickness and dried at room temperature. The transparent elastic and flexible film can be easily peeled off the glass and handled as needed. Films having an alginic acid to pilocarpine ratio of 1 to 12 are prepared, punched to fit inside the reservoir, and then the second barrier film laminated to the assembly.

EXAMPLE 4

An ocular insert consisting of a pre-punched colored ethylene-vinyl acetate film with an inwardly disposed hole, a pilocarpine polysaccharide film punched to fit inside the hole and two films placed on the platten in a laminator machine. The machine is closed and a vacuum equivalent to 29 inches of Hg is held for 3 minutes. At the end of 3 minutes, a radient heater is turned on and allowed to warm up for 15 seconds. The heater is then positioned between the plattens and the surface of the film heated to 70° C. The heater is then removed and the plattens are pushed together, with approximately 30 pounds of force. The plattens remain together under pressure of 30 pounds for 45 seconds while the film cools. The vacuum is then released and the plattens returned to their original position. Then, the machine is opened, the pilocarpine polysaccharide solid film deposited in the cavity and the remaining clear ethylene-vinyl acetate film placed over the exposed surface of the second wall. The three walls are returned to the laminator and the process repeated to yield the finished laminate.

EXAMPLE 5

The procedure of Example 4 is repeated in this example with all conditions as described except the polysaccharide gellation agent is replaced with the following polysaccharide filmation agents: agar, agarose, kappa-carrageenan and hypnean.

EXAMPLE 6

Following the procedure set forth in Example 1, an ocular drug delivery device shaped like a circle 6 mm × 2.5 mm is prepared according to the described procedure, except one of the drug delivery walls is formed from commercially available nylon-66, the dye is FDA approved red, and the drug in the reservoir is hydrocortisone alcohol. The area of the device is 1 $cm^2$ and the walls are 2 mils thick with the drug release rate for the ethylene-vinyl acetate copolymer wall about 40 micrograms per hour and the drug release rate for the nylon wall about 2 micrograms per hour.

EXAMPLE 7

Following the procedure set forth in Examples 1 and 2, an ocular drug delivery device is prepared wherein one drug release rate wall is cellulose acetate, the middle wall is ethylene-vinyl acetate copolymer and is dye-free, and the other drug release rate wall is silicone rubber. The drug release rate for hydrocortisone alcohol through a 1 $cm^2$ area wall that is 2 mils thick, is 3 micrograms per hour for the cellulose acetate wall, and 200 micrograms per hour for the silicone rubber drug release rate wall.

EXAMPLE 8

An ocular drug delivery device of banana shape, 21 mm × 5 mm × 0.25 mm, for administering a drug to the eye over prolonged periods of time at a controlled and continuous drug metered rate, is prepared as follows: a drug-carrier mix is first prepared by mixing liquid polydimethylsiloxane with 2000 micrograms of hydrocortisone alcohol and stannous octoate catalyst, 0.5 percent by weight, with the mixture charged into a preshaped banana mold having dimensions that correspond to the reservoir area of an ocular drug delivery device. The drug-steroid carrier is allowed to cure at room temperature and then removed from the mold. Next, the drug-steroid carrier is placed into the reservoir area of an ocular device that is comprised of a drug release rate controlling cellulose acetate wall having bonded onto its internal surface an ethylene-vinyl acetate banana shaped ring. Then, a second cellulose acetate release rate wall is heat sealed under vacuum and pressed onto the exposed surface of the ethylene-vinyl acetate ring to yield the ocular drug delivery device. The drug delivery walls are characterized by a porosity of 60 percent, a pore size of 0.45 micron and a thickness of 4 mils. When the device is inserted in the cul-de-sac of the conjunctiva between the sclera of the eyeball and the lower lid, the device delivers steroid at a controlled and therapeutically effective rate of drug to the eye for 24 hours of treatment.

EXAMPLE 9

A drug delivery device for the administration of a drug to the eye is manufactured in a retangular shape by laminating according to the procedure of Example 1. The device is made by laminating to the outer marginal area of an inner ethylene-vinyl acetate wall having a space in its central area, two outer walls wherein one wall consists of cellulose butyrate and the other wall poly(propylene) to define between the two outer walls and interior drug holding space for containing a pharmaceutical composition comprised of a drug and a drug carrier.

EXAMPLE 10

A device for releasing chloroamphenicol to the eye at a controlled rate is prepared as follows: first an elliptical ring 5 mm by 8 mm by 8–9 mils thick is punched-out from ethylene-vinyl acetate copolymer marketed as Elvax 40 by DuPont. This ring is laminated to a sheet of 3 mil Elvax 40 to form an open-topped container. Into this container is placed about 8 microliters of a suspension of 25 percent solid chloramphenicol in a saturated solution in polyethylene glycol. A second sheet of 3 mil Elvax 40 is laminated on top to close the container. The ocular insert when placed in an eye, releases 20 micrograms/hour of chloroamphenicol.

Thus, the novel ocular drug delivery device of this invention employs a unique means which facilitates the obtainment of precisely controlled drug release rates. While there have been described and pointed out the fundamental novel features of the invention as applied to the preferred embodiment, those skilled in the art will appreciate that various modifications, changes and omissions in the ocular drug delivery device illustrated and described can be made without departing from the spirit of the invention.

I claim:

1. An ocular device for the administration of drug comprising a three layered laminate having a pair of separate and discrete first and third walls formed of a material insoluble in tear fluid with one of the walls formed of a drug release rate controlling material permeable to the passage of drug and the other wall formed of a material impermeable to the passage of drug, a second wall interposed between the first and third walls and formed with an inwardly disposed hole with the second wall sealingly engaging the first and third walls to form a reservoir containing a drug selected from the group consisting of antibiotic, antibacterial, antiviral, antiallergenic, anti-inflammatory, miotic, anticholinesterase, mydriatic and sympathomimetic drugs, and wherein drug is administered from the device at a controlled and continuous rate by passage through the rate controlling wall over a prolonged period of time.

2. The ocular device for the administration of drug according to claim 1 wherein the antibiotic is a member selected from the group consisting of tetracycline, chlortetracycline, bacitracin, neomycin, polymyxin, gramicidin, oxytetracycline, chloramphenicol, gentamycin, penicillin, erythromycin, and mixtures thereof.

3. The ocular system for the administration of drug according to claim 1 wherein the antibacterial is a member selected from the group consisting of sulfonamide, sulfacetamide, sulfamethizole, sulfisoxyazole, and mixtures thereof.

4. The ocular system for the administration of drug according to claim 1 wherein the antiviral drug is idoxuridine.

5. The ocular device for the administration of drug according to claim 1 wherein the anti-inflammatory drug is a member selected from the group consisting of hydrocortisone, hydrocortisone acetate, dexamethasone, dexamethasone 21-phosphate, flucoinolone, medrysone, prednisolone, methylprednisolone, prednisolone 21-phosphate, prednisolone acetate, fluoromethalone, betamethasone and triaminolone.

6. The ocular device for the administration of drug according to claim 1 wherein the sympathomimetic is a member selected from the group consisting of phenylephrine, epinephrine and hydroamphetamine.

7. The ocular device for the administration of drug according to claim 1 wherein the drug release rate controlling wall is formed of a homogenous material permeable to the passage of drug by diffusion.

8. The ocular device for the administration of drug according to claim 1 wherein the reservoir containing the drug additionally contains a carrier which carrier is more permeable to the passage of drug than is the drug release rate controlling wall.

9. The ocular device for the administration of drug according to claim 1 wherein the second wall is formed of a member selected from the group consisting of poly(vinylacetate), cross-linked poly(vinyl alcohol), cross-linked poly(vinyl butyrate), ethylene-ethylacrylate copolymer, poly(ethyl hexylacrylate), poly(vinyl chloride), poly(vinyl acetate), ethylene-vinyl acetate copolymer, plasticized ethylene-vinyl acetate copolymer, poly(vinyl ester), poly(vinyl formal), and polyamide.

10. The ocular device for the administration of drug according to claim 1 wherein the drug is mixed with a carrier selected from the group of solid, semi-solid, liquid, gel and colloidal carriers.

11. The ocular device for administering drug according to claim 1 wherein the drug is mixed with a carrier selected from the group consisting of a polysaccharide, agar, agarose, algin, sodium alginate, carrageenan, fucordan, furcellaran, laminaran, hypnea, gum arabic, gum ghatti, gum karaya, starch, gum tragacanth, guar gum, locust bean gum, quince psyllium, okra gum, pectin, dextran, amylose, amylopectin, dextrin, cellulose, methylcellulose, hydroxyalkyl cellulose wherein the alkyl contains 1 to 7 carbon atoms, sodium carboxymethylcellulose, sodium carboxyethylcellulose, ethylcellulose, and mixtures thereof.

12. The ocular device for administering drug according to claim 1 wherein the device has a geometric shape selected from the group consisting of ring, bean, elliptical, banana, rectangular, square, trapezoidal, triangular, half-circle and crescent shaped devices.

13. An ocular device for the administration of an ophthalmic drug comprising a three layered laminate having a pair of separate and discrete first and third walls formed of a material insoluble in tear fluid with one of the walls formed of a drug release rate controlling material permeable to the passage of drug and the other wall formed of a material impermeable to the passage of drug, a second wall interposed between the first and third walls and formed with an inwardly disposed hole with the second wall sealingly engaging the first and third walls to form a reservoir containing a drug selected from the group of ophthalmic drugs consisting of pilocarpine, pilocarpine and its acceptable salts, eserine salicylate, carbachol, eserine, phospholine iodide, demecarium bromide, cyclopentolate, homatropine, scopolamine, atropine, atropine sulfate, eucatropine, and tropicamide.

14. An ocular device for the administration of drug comprising a three layered laminate having a pair of separate and discrete first and third walls formed of a material insoluble in tear fluid with one of the walls formed of a microporous material, the pores of which contain a drug release rate controlling medium permeable to the passage of drug and the other wall formed of a material impermeable to the passage of drug, a second wall positioned between the first and third walls and formed with an inwardly disposed hole with the second wall sealingly engaging the first and third walls to form a reservoir containing a drug selected from the group consisting of antibiotic, antibacterial, antiviral, antiallergenic, anti-inflammatory, miotic, anticholinesterase, mydriatic and sympathomimetic drugs, and wherein drug is administered from the device at a controlled and continuous rate by passage through the rate controlling medium over a prolonged period of time.

15. An ocular device for the administration of drug according to claim 14 wherein the drug is an ophthalmic drug selected from the group consisting of pilocarpine, pilocarpine and its acceptable salts, eserine, eserine salicylate, carbachol, phospholine iodide, demecarium bromide, cyclopentolate, homatropine, scopolamine, atropine, atropine sulfate, eucatropine and tropicamide.

16. An ocular system for the administration of drug according to claim 14 wherein the microporous wall is formed of a microporous material having a porosity of between 5 percent and 95 percent.

17. An ocular delivery device for the continuous administration of drug over a prolonged period of time comprising a sealed container shaped for insertion and placement in the eye, said container comprising a pair of first and third membrane walls spaced from each other, each formed of a material insoluble in ocular fluid with one of the membrane walls formed of a material permeable to the passage of ocular drug and the other membrane wall formed of a material substantially impermeable to the passage of drug, a second peripheral shaped wall interposed between and sealingly engaging the first and third membrane walls along their outer faced peripheries to define an integral unit and form a reservoir defined by the inner surface of the first, second and third walls, said reservoir containing ocular drug selected from the group consisting of locally and systemically acting drugs which are released therefrom at a controlled and continuous rate by passage through the release rate controlling membrane wall over a prolonged period of time.

18. The ocular delivery device for the continuous administration of ocular drug according to claim 17 wherein the second wall is ring, elliptical, oval or annular shaped.

19. The ocular delivery device for the continuous administration of ocular drug according to claim 17 wherein the device is longer than wide and is designed for insertion and placement in the cul-de-sac of the eye.

20. An ocular delivery device for the continuous administration of ocular drug according to claim 17 wherein the drug is a member selected from the group consisting of antibiotic, antibacterial, antiviral, antiallergenic, anti-inflammatory, miotic, anticholinesterase, mydriatic and sympathomimetic drugs.

21. An ocular delivery device for the continuous administration of drug according to claim 17 wherein the drug is a member selected from the group consisting of phenylephrine, epinephrine, pilocarpine, pilocarpine and its acceptable salts, eserine, idoxuridine, tetracycline, neomycin, penicillin, erythromycin, scopolamine, atropine, physostigmine, hydrocortisone, prednisolone, and sulfisoxazole.

22. An ocular delivery device for the continuous administration of drug according to claim 17 wherein the membrane wall is formed of a material permeable to the passage of ocular drug by diffusion selected from the group consisting of ethylene-vinyl acetate copolymer, plasticized ethylene-vinyl acetate copolymer, poly(dimethylsiloxane) and poly(ethylene).

23. An ocular delivery system for the continuous administration of drug according to claim 17 wherein the device is sized, shaped and adapted for insertion and placement into a human eye and has a length of 4 to 20 millimeters, a width of 1 to 15 millimeters and a thickness of 0.1 to 4 millimeters.

24. An ocular delivery device for the continuous administration of drug according to claim 17 wherein the reservoir has a diameter of 1.2 to 14.8 millimeters and contains from 1 microgram to 100 milligrams of ocular drug.

25. An ocular delivery device for the continuous administration of drug comprising a closed container shaped and sized for insertion and placement in the eye, said container comprising a pair of first and third walls spaced from each other, each formed of a material insoluble in ocular fluid with one of the walls formed of a microporous polymeric material capable of housing in its pores a drug release rate controlling medium permeable to the passage of drug and the other wall formed of a material substantially impermeable to the passage of drug, a second peripheral shaped wall positioned between and sealingly engaging the first and third walls along their marginal faced peripheries to define an integral unit and form a reservoir defined by the inner surface of the first, second and third walls, said reservoir containing an ocular drug selected from the group of drugs that give physiologic and pharmacologic beneficial effects, which is released from the device at a controlled and continuous rate by passage through the release rate controlling medium housed in the pores over a prolonged period of time.

26. The ocular delivery device for the continuous administration of drug according to claim 25 wherein the drug has limited solubility in the medium housed in the pores with the drug selected from the group consisting of mydriatic, parasympatholytic, parasympathomimetic, anticholinesterase, adrenergic, anti-inflammatory, anti-infective, antifungal and antiviral drugs.

27. The ocular delivery device for the continuous administration of drug according to claim 25 wherein the medium housed in the micropores is eye fluid.

* * * * *